United States Patent [19]

Tracy et al.

[11] 4,138,571
[45] Feb. 6, 1979

[54] NITROPHENYL IMINO PROPIONATES

[75] Inventors: David J. Tracy, Lincoln Park, N.J.; Walter F. Hoffstadt, Vestal, N.Y.

[73] Assignee: GAF Corporation, New York, N.Y.

[21] Appl. No.: 742,011

[22] Filed: Nov. 15, 1976

[51] Int. Cl.² ............................................ C07C 119/20
[52] U.S. Cl. ........................................ 560/22; 560/35
[58] Field of Search ........................ 260/471 A, 310 A

[56] References Cited

U.S. PATENT DOCUMENTS

| 3,798,234 | 3/1974 | Meier | 260/310 A |
| 3,939,176 | 2/1976 | Gandino | 260/310 A |
| 3,979,412 | 9/1976 | Arai | 260/310 A |

FOREIGN PATENT DOCUMENTS

| 2304587 | 8/1974 | Fed. Rep. of Germany. |
| 1469360 | 2/1967 | France. |
| 1129334 | 10/1968 | United Kingdom. |

OTHER PUBLICATIONS

Post, Howard, "The Chemistry of Aliphatic Orthoesters", 1943, p. 23.

*Primary Examiner*—Donald G. Daus
*Assistant Examiner*—Lisa Jones
*Attorney, Agent, or Firm*—W. C. Kehm; Walter Katz

[57] ABSTRACT

A feature of the present invention is the provision of imidic esters having halo and nitro substituents on the phenyl ring attached to the nitrogen atom of the imidic ester, and of a method for preparing such compounds in high yields. In accordance with the process of the present invention, it has been found that imidic esters can be prepared in high yields using available starting materials. In the process, an alkyl β-alkoxy-β-iminopropionate salt is reacted first with a suitable alkanol to form an orthoester intermediate in situ. Then the orthoester is converted in high yields to the corresponding imidic ester by condensation with an aniline while simultaneously removing alkanol from the reaction mixture to drive the equilibrium reaction to completion. In a preferred form of the invention, the formation of the imidic ester is carried out in a high boiling solvent whose presence enables the condensation to be carried out more effectively at a high temperatue than with alkanol alone. Particularly, the high boiling solvent mixture adds volume to the reaction mixture which enables good agitation of the reactants at a predetermined and measureable reaction temperature. Furthermore, it facilitates the simultaneous distillation of the more volatile alkanol by-product from the reaction mixture.

2 Claims, No Drawings

NITRPOPHENYL IMINO PROPIONATES

BACKGROUND OF THE INVENTION

This invention relates to imidic esters and to a method of preparation thereof.

This application is a continuation-in-part of application Ser. No. 603,533, filed Aug. 11, 1975.

3-anilino-5-pyrazolones are intermediates in the manufacture of pyrazolones such as 2-pyrazolin-5-ones, which are used as magenta color formers in photographic color materials. The 3-anilino-5-pyrazolones may be prepared by a multi-step process in which imidic esters are formed as intermediates.

Accordingly, it is an object of the present invention to provide an improved method for making imidic esters, and more particularly, to provide certain imidic esters which may be utilized as intermediates in the manufacture of particularly high quality pyrazolone color formers which have proven especially difficult to make in high yields by other methods or techniques known in the art.

DESCRIPTION OF THE PRIOR ART

Several methods are described in the literature for preparing imidic ester intermediates, including the U.S. Pat. No. 3,798,234 and Brit. Nos. 1,129,333, 1,129,334 and 1,134,329, but these are severely limited with respect to the substituent groups which may be made a part of the imidic ester, or as to the yield and economy of manufacture of the desired product.

SUMMARY OF THE INVENTION

A feature of the present invention is the provision of imidic esters having halo and nitro substituents on the phenyl ring attached to the nitrogen atom of the imidic ester, and of a method for preparing such compounds in high yields.

In accordance with the process of the present invention, it has been found that imidic esters can be prepared in high yields using available starting materials. In the process, an alkyl $\beta$-alkoxy-$\beta$-iminopropionate salt is reacted first with a suitable alkanol to form an orthoester intermediate in situ. Then the orthoester is converted in high yields to the corresponding imidic ester by condensation with an aniline while simultaneously removing alkanol from the reaction mixture to drive the equilibrium reaction to completion. In a preferred form of the invention, the formation of the imidic ester is carried out in a high boiling solvent whose presence enables the condensation to be carried out more effectively at a high temperature than with alkanol alone. Particularly, the high boiling solvent mixture adds volume to the reaction mixture which enables good agitation of the reactants at a predetermined and measurable reaction temperature. Furthermore, it facilitates the simultaneous distillation of the more volatile alkanol byproduct from the reaction mixture.

To convert the imidic ester intermediate to the 3-anilino-5-pyrazolone, the following additional steps are followed. The solid ammonium halide by-product of the reaction removed by filtration and the resulting imidic ester solution is reacted with a hydrazine to form the corresponding amidine compound. The amindine then is cyclized to provide the desired 3-anilino-5-pyrazolone. This sequence of steps, in combination, provides the useful pyrazolones in high yields and in relatively low cost. A particular feature of the overall process as described is that no isolation of intermediates or change of solvent is necessary during the several steps of the process.

DESCRIPTION OF THE PREFERRED EMBODIMENTS

The imidic esters prepared according to the novel process of the invention have the general formula:

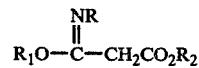

Where $R_1$ and $R_2$ are lower alkyl, and
R is phenyl or a phenyl substituted with one or more of halo, nitro, and alkoxy, and combinations thereof.

Accordingly, suitable R groups include phenyl; a nitrophenyl, such as 4-nitrophenyl and 3-nitrophenyl; a halophenyl, such as 2-chlorophenyl, 2-bromophenyl, 2,6-dichlorophenyl, 2,4,5-trichlorophenyl, 2,4,6-trichlorophenyl, 3,5-dibromophenyl and 4-fluorophenyl; and alkoxyphenyl, such as 2-ethoxyphenyl and 4-butoxyphenyl; and combinations thereof, such as halonitrophenyl, such as 2-chloro-5-nitrophenyl and 2-chloro-4-nitrophenyl.

In a preferred embodiment of the invention, R is a phenyl group substituted with a halo and a nitro group, which is particularly useful in making 2-pyrazolin-5-one color formers, which have a sharp absorption peak at the desired wavelength, and a minimum of side absorbances.

The presence of the nitro group in the imidic ester enables various acyl groups to be added to the molecule by reduction of the nitro to amino and subsequent acylation. A halo substituent in the phenyl ring, which can hydrogen bond with the nitrogen atom to which the phenyl group is attached, can serve to prevent rotation of the phenyl ring, thereby decreasing the width of the absorption peak of the color former compound.

A suitable starting material for the process of the invention is an alkyl $\beta$-alkoxy-$\beta$ iminopropionate salt having the general formula:

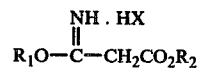

Where $R_1$ and $R_2$ are lower alkyl, which may be same or different, and X is a halogen;
which may be prepared by the reaction of the corresponding nitrile with an appropriate alkanol and hydrogen halide, as described in Ber. 87, 205 (1954). Ethyl $\beta$-iminopropionate hydrogen chloride, for example, may be prepared by reaction of ethyl $\beta$-cyanopropionate, ethanol and hydrogen chloride.

In the first step of the process of the invention, the alkyl $\beta$-alkoxy-iminopropionate salt is contacted with a primary or secondary lower alkanol to form an orthoester intermediate in situ. The lower alkanol must be a nonhindered alkanol, that is , a primary or secondary lower alkanol (i.e. not a tertiary alkanol) so that the reaction between iminopropionate and alkanol can proceed satisfactorily to the orthoester stage. Both the lower alkanol and the alkoxy group of the iminopropionate may be selected from $C_1$–$C_4$ groups, which may be the same or different. Thus the three alkoxy groups of the resulting orthoester can be either all the same (e.g., trimethoxy, triethoxy, etc.) or else they can be different, depending upon the respective nature or identity of the alkoxy group and of the alkyl moiety of the alkanol reactant.

This reaction may be carried out in the alkanol reactant, which can then act as a solvent in the reaction, or, preferably, in a solvent admixture which includes a high boiling component, as will be described in detail hereinafter.

Reaction between the iminopropionate and alkanol is carried out at ambient temperatures, suitably at room temperature for about 12-24 hours.

Once the orthoester is formed in situ, it is directly converted to corresponding imidic ester by condensation with a suitable aniline. As a feature of the present invention, this reaction is carried out while simultaneously removing two moles of alkanol by-product from the reaction mixture, thereby providing the desired imidic ester in high yields, according to the following equations:

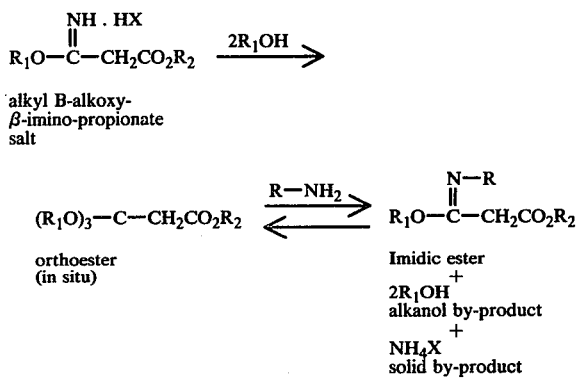

where $R_1$ and $R_2$ are as previously defined, and
R is phenyl or phenyl substituted with one or more substituents selected from nitro, halo and alkoxy, and combinations thereof.

Removal of the alkanol by-product in the manner described drives the equilibrium reaction between orthoester and aniline to completion, thus substantially increasing the yield of the desired imidic ester.

As noted, condensation between the orthoester and the phenylamine preferably is carried out in the presence of a high boiling solvent for said reactants. The high boiling solvent enables the condensation reaction to proceed at an elevated temperature, and facilitates the removal of the lower boiling alkanol by-product by distillation at atmospheric pressure, thereby increasing the yield of imidic ester. Suitable high boiling solvents are those in which the reactants are inert and wholly miscible or soluble, and which have a boiling point higher than the alkanol itself, so as to enable the latter to be efficiently removed in the presence of the former. Typical solvents which satisfy these criteria have boiling points between about 80° C. and about 150° C., and are usually selected from among aromatic and aliphatic hydrocarbons and halogenated hydrocarbons, such as benzene, toluene, xylene, chlorobenzene, dichlorobenzene, tetrachloroethylene, tetrachloroethane and the like.

In a typical run, the imidic ester is formed advantageously by progressively heating the orthoester and phenylamine up to a reaction temperature of about 90°-120° C., while simultaneously removing two moles of the alkanol by-product by distillation at atmospheric pressure. Preferably, the reactants are heated up to about 110° C. during a period of about 3 or 4 hours, and then held at 110° C. for about ½ hour, during which heating periods alkanol is being distilled off continuously.

Of course, the high boiling solvent may be included initially in the charge of reactants which are used to form the orthoester, i.e., the iminopropionate and alkanol, and thus be ready for the next stage.

Solid ammonium halide, e.g., ammonium chloride, which is deposited during the course of the reaction as a by-product, then is filtered off to provide the imidic ester in the filtrate ready for isolation by crystallization, or for direct use in the next step in the overall process.

Representative non-limiting examples of unsubstituted of substituted anilines suitable for use include the following: aniline; o-, m-, or p-chloroaniline; o-, m-, or p-bromoaniline; o-, m-, or p-nitroaniline; 2,3-, 2,5-, 2,6-dibromoaniline; 2,3-, 2,4-, 2,5-, 2,6-, 3,4-, or 3,5-dichloroaniline; 2-chloro-4-nitroaniline; 2-chloro-5nitroaniline; 4-chloro-2-nitroaniline; 4-chloro-3-nitroaniline; 2-methoxy-4-nitroaniline; 2-methoxy-5-nitroaniline; 4-methoxy-2-nitroaniline; 2,4-dinitroaniline; 2,6-dinitroaniline; 3,5-dinitroaniline 2,5-dichloro-4-nitroaniline; 2,6-dichloro-4-nitroaniline; 4,5-dichloro-2- nitroaniline; 2,4,6-trichloroaniline; 4-fluoro-2-nitroaniline; and 4-fluoro-3nitroaniline. The preferred aniline is 2chloro-5-nitroaniline.

To complete the overall process to provide the 3-anilino-5-pyrazolone, the imidic ester solution is reacted with a phenylhydrazine to form an amidine in accordance with the following equation:

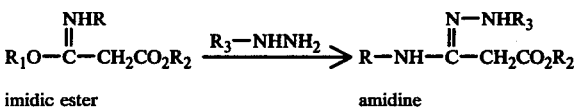

where $R_3$ is phenyl or phenyl substituted with one or more of halo, nitro and alkoxy, and combinations thereof Accordingly, $R_3$ groups in the hydrazine reactant include phenyl; a halophenyl, e.g., 2chlorophenyl, 2-bromophenyl, 2,6-dichlorophenyl, 2,4,5-trichlorophenyl, 2,4,6-trichlropheynl, 3,5-dibromophenyl and 4-fluorophenyl; a nitrophenyl, e.g., 4-nitrophenyl and 3-nitrophenyl; and alkoxy, e.g. 2-ethoxyphenyl and 4-butoxyphenyl, and combinations thereof, such as 2-chloro-5-nitrophenyl, and 2-chloro-4-nitrophenyl.

The amidines thus-prepared then are converted to the desired 3-anilino-5-pyrazolones by reaction with a cyclization agent which effects ring closure of the amidine. Suitably, from one to two molar equivalents of the cyclization agent is used for this purpose. The cyclization agent usually is a base, e.g. an alkali, an alkaline earth or a metal $C_1$-$C_5$ alkoxide.

Specific applications of the compositions and processes of the present invention and the various alternative embodiments thereof are further illustrated by the examples which follow. The specific details of these examples are not to be taken as limitations upon the invention.

EXAMPLE I

Ethyl β-methoxy-β-(2-chloro-5-nitrophenylimino)propionate

To a flask equipped with stirrer and condenser are charged: 156.0 g (0.8 mole of ethyl-3-iminopropionate hydrochloride. 103.0 g (0.6 mole 2- chloro-5-nitroaniline, and 500 ml reagent grade methanol (anhydrous). The resulting mixture is stirred at room temperature (ca. 20° C.) for 20 hours, whereupon it is heated to reflux for one hour while being concentrated to a pot temperature of 100° C. while distilling off methanol at atmospheric pressure, cooled to room temperature, and ammonium chloride filtered off. The resulting salt is washed well with 200 ml of methanol (water free) and the filtrate cooled. The product is filtered to yield 84.6 g (47%), and recrystallized from isopropanol-heptane (50/50 by volume), to yield a product having a melting point of 60–62° C.

Infra-red analysis revealed the ester linkage at 1735, a band at 1670, (C=N) and the absence of NH absorption. The NMR exhibited a methoxy singlet and agreed with the product structure identified above.

Anal. Calculated for $C_{12}H_{13}ClN_2O_5$: C,47.92%; H,4.35%; Cl, 11.79%; and N, 9.32%. Found: C,47.81%; H,4.32%; Cl, 11.95%; N,9.29%.

The process of Example I is followed except that 250 ml of tolune solvent is included in the charge. The same imidic ester product is obtained in a 65% yield.

EXAMPLE II

Ethyl-β-methoxy-β-(4-nitrophenylimino) propinoate

The method of Example I is followed with a charge of 156 g (0.8 mole) of ethyl-3-ethoxy-3-iminopropionate hydrochloride. 82.2 g of (0.6 mole) p-nitroaniline, and 500 ml methanol to give a crude product yield of 109 g (69% of theory) which upon recrystallization from isopropanol-water, gave the above-identified product with a melting point of 104–108° C., and whose structure was confirmed by infra-red and NMR spectroscopy.

Anal. Calculated for $C_{12}H_{14}N_2O_5$; C,54.13%; H,5.20%; N,10.52%. Found: C, 54.26%; H,5.26%; N, 10.49%.

The process of Example II is followed except that 250 ml. of toluene is included in the charge. The same product is obtained in high yield.

EXAMPLE III

Ethyl-β-ethoxy-β-(2-chloro-5-nitrophenylimino) propionate

To a flask equipped with stirrer, condenser and thermometer are charged: 97.0 g (0.5 mole) of ethyl 3-ethoxy-3-iminopropionate hydrochloride, 51.5 g (0.3 mole) of 2-chloro-5-nitroaniline, and 500 ml of anhydrous methanol. These ingredients are stirred at room temperature overnight, and the methanol is distilled off to a temperature of 105° C. The resultant salt (21.4 g) is filtered and the desired product is crystallized.

EXAMPLE IV

Ethyl-β-methoxy-β-(3-nitrophenylimino) propionate

The process of Example I, with addition of toluene solvent is followed using m-nitroaniline to provide the corresponding imidic ester in high yield.

EXAMPLE V

Ethyl-β-methoxy-β-(2-chloro-4-nitrophenylimino) propionate

The process of Example I, with addition of toluene solvent, is followed using 2-chloro-4-nitroaniline to provide the corresponding imidic ester in high yield.

EXAMPLE VI

Ethyl-β-methoxy-β-(2,4-dichlorophenylimino) propionate

The process of Example I, with addition of toluene solvent is followed using 2,4-dichloroaniline to provide the corresponding imidic ester in high yield.

It should be understood from the foregoing that the above description is merely illustrative of the perferred embodiments and specific examples of the present invention and that in all of which embodiments and examples, variations, such as, e.g., those previously described, can be made by those skilled in the art without departing from the spirit and purview thereof, the invention being defined by the following claims.

What is claimed is:
1. Ethyl β-ethoxy-β-(2-chloro-5-nitrophenylimino) propionate.
2. Ethyl β-methoxy-β-(2-chloro-5-nitrophenylimino) propionate.

* * * * *